(12) United States Patent
Sousa et al.

(10) Patent No.: US 9,778,207 B2
(45) Date of Patent: Oct. 3, 2017

(54) INTEGRATED MULTI-PASS INSPECTION (71) Applicant: KLA-Tencor Corporation, Milpitas, CA (US)

(72) Inventors: Weston L. Sousa, San Jose, CA (US); Yalin Xiong, Pleasanton, CA (US); Rui-Fang Shi, Cupertino, CA (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

(21) Appl. No.: 14/890,880

(22) PCT Filed: May 14, 2014

(86) PCT No.: PCT/US2014/038017
§ 371 (c)(1),
(2) Date: Nov. 12, 2015

(87) PCT Pub. No.: WO2014/186476
PCT Pub. Date: Nov. 20, 2014

(65) Prior Publication Data
US 2016/0093040 A1 Mar. 31, 2016
US 2017/0256043 A9 Sep. 7, 2017

Related U.S. Application Data (60) Provisional application No. 61/823,269, filed on May 14, 2013.

(51) Int. Cl.
G01N 21/88 (2006.01)
G03F 1/84 (2012.01)
(Continued)

(52) U.S. Cl.
CPC ....... *G01N 21/8851* (2013.01); *G01N 21/956* (2013.01); *G01N 21/95607* (2013.01);
(Continued)

(58) Field of Classification Search
CPC ........ G06T 2207/30148; G06T 7/0002–7/001; G01N 2021/95676
See application file for complete search history.

(56) References Cited

U.S. PATENT DOCUMENTS 7,003,177 B1  2/2006  Mendlovic et al.
7,873,204 B2  1/2011  Wihl et al.
(Continued)

FOREIGN PATENT DOCUMENTS

WO  2008/086528  7/2008
WO  2012/030825  3/2013
WO  2012/030830  3/2013

OTHER PUBLICATIONS

International Search Report and Written Opinion for PCT/US2014/038017 mailed Jan. 29, 2015.
(Continued)

*Primary Examiner* — Stephen R Koziol
*Assistant Examiner* — Raphael Schwartz
(74) *Attorney, Agent, or Firm* — Ann Marie Mewherter (57) ABSTRACT

Methods and systems for integrated multi-pass reticle inspection are provided. One method for inspecting a reticle includes acquiring at least first, second, and third images for the reticle. The first image is a substantially high resolution image of light transmitted by the reticle. The second image is a substantially high resolution image of light reflected from the reticle. The third image is an image of light transmitted by the reticle that is acquired with a substantially low numerical aperture. The method also includes detecting defects on the reticle using at least the first, second, and third images for the reticle in combination.

37 Claims, 3 Drawing Sheets

(51) Int. Cl.
*G06T 7/00* (2017.01)
*G01N 21/956* (2006.01)

(52) U.S. Cl.
CPC ............ *G03F 1/84* (2013.01); *G06T 7/001* (2013.01); *G01N 2021/95676* (2013.01); *G01N 2201/12* (2013.01); *G06T 2207/30148* (2013.01)

(56) References Cited

U.S. PATENT DOCUMENTS

| | | | |
|---|---|---|---|
| 7,907,270 B2 | 3/2011 | Kusunose | |
| 8,103,086 B2 | 1/2012 | Shi et al. | |
| 8,611,637 B2 | 12/2013 | Shi et al. | |
| 2001/0019625 A1 | 9/2001 | Kenan et al. | |
| 2006/0287751 A1* | 12/2006 | Dishner | G05B 23/0221 700/110 |
| 2008/0018883 A1 | 1/2008 | Kvamme et al. | |
| 2008/0170773 A1 | 7/2008 | Wihl et al. | |
| 2008/0304056 A1* | 12/2008 | Alles | G03F 1/84 356/237.5 |
| 2011/0149331 A1 | 6/2011 | Duggan et al. | |
| 2011/0317136 A1* | 12/2011 | Ryzhikov | G03F 1/84 355/30 |
| 2012/0086799 A1 | 4/2012 | Hess | |
| 2013/0077086 A1 | 3/2013 | Chuang et al. | |

OTHER PUBLICATIONS

International Preliminary Report on Patentability for PCT/US2014/038017 mailed Nov. 26, 2015.

\* cited by examiner

INTEGRATED MULTI-PASS INSPECTION

BACKGROUND OF THE INVENTION

1. Field of the Invention

This invention generally relates to the field of reticle inspection. More particularly, the present invention relates to a method of integrated multi-pass inspection of a reticle.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing (CMP), etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on reticles to promote higher yield in the manufacturing process and thus higher profits. Inspection has always been an important part of fabricating semiconductor devices such as ICs. However, as the dimensions of semiconductor devices decrease, inspection becomes even more important to the successful manufacture of semiconductor devices.

In general, existing methods for reticle inspection utilize one of two imaging modes to inspect a mask. The most common inspection mode known as reticle plane inspection (RPI) involves capturing high resolution transmitted and reflected images of a reticle and processing the two images together. The resolution is much higher than that of the wafer scanner used to print the reticle images to the wafer. The Teron™ platform designed, manufactured, and marketed by KLA-Tencor, Milpitas, Calif. is the industry standard inspection tool for RPI inspection modes. This type of inspection has the best performance for finding relatively small point defects. As optical proximity correction (OPC) gets more complex, it can be challenging to use this inspection mode to differentiate between primary features, where defect detection sensitivity needs to be high due to the criticality of the primary features, and assist features, where defect detection sensitivity can be lower due to the non-criticality of these features. It can also be challenging to use this inspection mode to separate non-wafer-printing nuisance defects on primary features from critical, wafer-printing defects due to the complex rules in geometry classification typically used in defect detection. In a die-to-die inspection, since database information is typically not used for defect detection, geometry classification can be even more difficult, which can make separating printing critical defects from non-printing nuisance defects challenging. Furthermore, this approach has difficulties finding diffuse and phase defects, which are becoming more common and important to catch.

Another inspection method called low numerical aperture (NA) inspection (LNI) involves a mode that emulates the wafer scanner optical conditions, capturing one image in transmitted light at a lower NA than RPI with illumination conditions that approximate the scanner's. Utilizing this method allows the system to differentiate between primary features with high sensitivity and assist features regardless of the reticle type or complexity of the underlying patterns on the reticle. It also enables estimating the printability impact of a defect on the wafer plane. Furthermore, LNI inspection mode readily detects diffuse and phase defects due to the optical conditions of the LNI mode. However, this mode has fundamentally lower resolution making it difficult to find relatively small point defects.

Another method for contamination inspection known as SL involves analyzing two images, RPI transmitted and reflected, to find defects that standout from the background pattern. This method can be challenged by more complex masks where the assist and optical proximity correction (OPC) patterns look substantially similar to the contamination that the defect detection algorithm is trying to detect.

Accordingly, it would be advantageous to develop methods and/or systems for reticle inspection that do not have one or more of the disadvantages described above.

SUMMARY OF THE INVENTION

The following description of various embodiments is not to be construed in any way as limiting the subject matter of the appended claims.

One embodiment relates to a method for inspecting a reticle. The method includes acquiring at least first, second, and third images for the reticle. The first image is a substantially high resolution image of light transmitted by the reticle. The second image is a substantially high resolution image of light reflected from the reticle. The third image is an image of light transmitted by the reticle that is acquired with a substantially low numerical aperture. The method also includes detecting defects on the reticle using at least the first, second, and third images for the reticle in combination. The acquiring and detecting steps are performed with one or more computer systems.

The method described above may be performed as described further herein. In addition, the method described above may include any other step(s) of any other method(s) described herein. Furthermore, the method described above may be performed by any of the systems described herein.

Another embodiment relates to a non-transitory computer-readable medium storing program instructions executable on a computer system for performing a computer-implemented method for inspecting a reticle. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

An additional embodiment relates to a reticle inspection system that includes one or more optical subsystems configured to acquire at least first, second, and third images for the reticle. The first image is a substantially high resolution image of light transmitted by the reticle. The second image is a substantially high resolution image of light reflected from the reticle. The third image is an image of light transmitted by the reticle that is acquired with a substantially low numerical aperture. The reticle inspection system also includes one or more computer subsystems configured for detecting defects on the reticle using at least the first, second, and third images for the reticle in combination. The reticle inspection system may be further configured as described herein.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

The embodiments described herein generally relate to integrated multi-pass reticle inspection. The embodiments described herein can be used to improve reticle inspection performance. Performance is defined as finding more defects of interest (DOIs) white limiting the number of false defects (i.e., those that do not exist) or nuisance defects (i.e., those that the reticle inspection system user does not care about). The embodiments described herein can be applied to inspections for detecting pattern and/or contamination type defects. In addition, the embodiments described herein can be applied to various types of defect detection such as cell-to-cell (CC), die-to-die (DD), die-to-database (DB), or STARlight (SL). The terms "reticle" and "mask" are used interchangeably herein and are intended to mean any reticle or mask known in the art that is used to transfer a pattern to another substrate such as a wafer.

As masks become more complex, it becomes increasingly more difficult to inspect the masks with a relatively low nuisance and/or false rate while maintaining sensitivity to DOIs. Furthermore, the types of defects that users need to catch to maintain yields on the wafers being fabricated using a reticle are becoming more diverse and difficult to detect with existing inspection strategies. The embodiments described herein address several limitations with existing approaches.

The embodiments described herein involve capturing three or more images for a reticle and processing them together to optimize the performance of the inspection mode. More specifically, one embodiment of a method for inspecting a reticle includes acquiring at least first, second, and third images for the reticle. The first image is a substantially high resolution image of light transmitted by the reticle. The second image is a substantially high resolution image of light reflected from the reticle. The third image is an image of light transmitted by the reticle that is acquired with a substantially low numerical aperture (NA). The method also includes detecting defects on the reticle using at least the first, second, and third images for the reticle in combination. The acquiring and detecting steps are performed with one or more computer systems, which may be configured as described further herein.

A "substantially high resolution image" as that term is used herein refers to an image of a reticle in which features printed on the reticle appear substantially as they are formed on the reticle (within the optical limitations of the reticle inspection system used to generate the image). For example, a "substantially high resolution image" of a reticle is an image that is generated by imaging the physical reticle at the reticle plane with a substantially high resolution reticle inspection system (e.g., a reticle inspection system capable of generating images with a substantially high NA (e.g., an NA of greater than 0.8)). In contrast, a "substantially low NA" used to generate the third image may be an NA that is less than 0.5. In addition, the "substantially low NA" used to generate the third image may be substantially the same as the NA on the reticle side that is used by an exposure system to project an image of the reticle onto a wafer thereby transferring features on the reticle onto the wafer. Therefore, in the substantially low NA image, the reticle features may appear substantially differently than they were formed on the reticle. For example, in the substantially low NA image, reticle features may appear to have more rounded corners than what was formed on the reticle.

Figure 1:
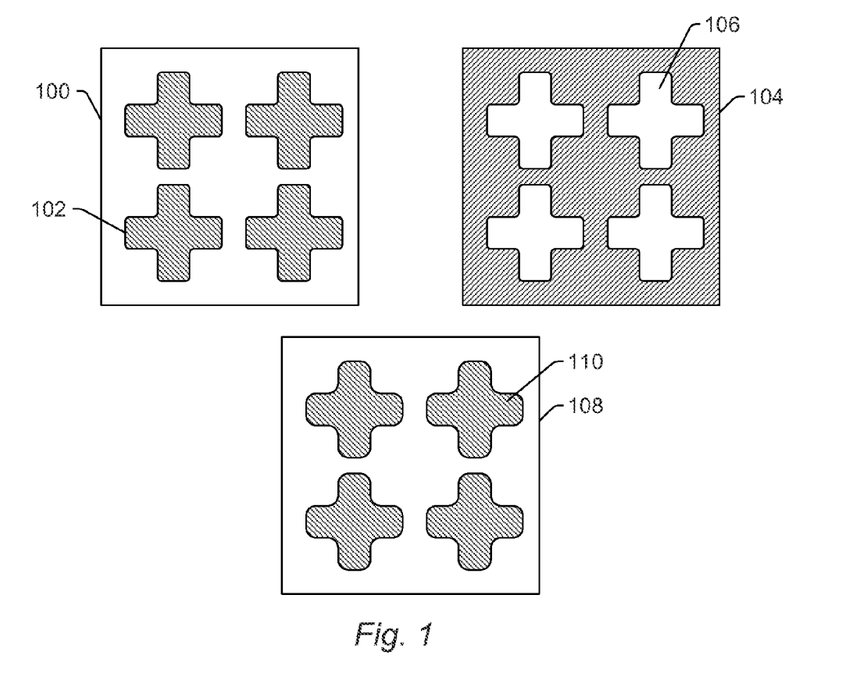
FIG. 1 is a schematic diagram illustrating a plan view of embodiments of first, second, and third images for a reticle.

To illustrate the differences between the different types of images, several hypothetical examples are shown in FIG. 1. In particular, image 100 may be a substantially high resolution image of light transmitted by a reticle. In this manner, image 100 may be used as a "first image" described herein. In this image, the white portions in FIG. 1 indicate the bright portions in the image. Therefore, the white portions indicate the high transmission areas of the reticle. In addition, dark portions 102 shown in the image indicate the dark portions in the image. As such, the dark portions indicate the low transmission areas of the reticle. Therefore, the dark portions correspond to opaque features formed on the reticle.

As shown further shown in FIG. 1, image 104 is a substantially high resolution image of light reflected by the same reticle. In this manner, image 104 may be used as a "second image" described herein. In this image, white portions 106 indicate the bright portions in the image, and the dark portions indicate the dark portions in the image. As such, white portions 106 correspond to the reflective, opaque features of the reticle while the dark portions correspond to the highly transmissive portions of the reticle.

FIG. 1 also includes image 108 that is an image of the same hypothetical reticle that is formed by light transmitted by the reticle and imaged with a substantially low NA.

Therefore, image 108 may be used as the "third image" described herein. The bright portions in this image correspond to the bright portions in image 100 since they are both generated by transmitted light. In addition, dark portions 110 of image 108 correspond to dark portions 102 of image 100. However, as can be seen by comparison of image 108 with images 100 and 104, since image 108 is acquired using a substantially low NA, the resolution of the features in the image is lower than that in images 100 and 104 that are acquired with substantially high resolution at the reticle plane. In addition, as described further herein, the NA used to generate the third image may be selected such that the third image approximates the aerial image that will be projected on a wafer by a lithography exposure system. Therefore, the third image may approximate the wafer plane image of a reticle.

Any of the images described herein of light transmitted by the reticle can, in some embodiments, include some reflected light. For example, a relatively small amount of reflected light can be blended with the light transmitted by the reticle and the resulting blended image can be used as the transmitted light image. In a similar manner, any of the images described herein of light reflected by the reticle can include some transmitted light. In particular, a relatively small amount of transmitted light can be blended with the light reflected by the reticle and the resulting blended image can be used as the reflected light image. Examples of methods and systems that can be used to produce such blended images are described in U.S. Pat. No. 7,907,270 issued on Mar. 15, 2011 to Kusunose, which is incorporated by reference as if fully set forth herein. The methods and systems may be further configured as described in this patent.

To utilize the approaches described herein, at least some of the first, second, and third images may be captured sequentially and at least some of the images may be stored in one or more storage media until all images are available for processing. For example, in one embodiment, acquiring at least the first, second, and third images for the reticle includes acquiring the first and second images from one reticle inspection system and acquiring the third image from another reticle inspection system. Such reticle inspection systems may be further configured as described herein. In this manner, different images can be acquired from different reticle inspection systems, which may be the case when any one reticle inspection system is not capable of acquiring all of the images described herein.

In another embodiment, this approach can be implemented by switching optical modes during inspection or running an entire inspection in one mode, followed by subsequent modes, and feeding these images together at the same time for processing. For example, in one embodiment, acquiring at least the first, second, and third images for the reticle includes acquiring the first, second, and third images from one reticle inspection system, and the one reticle inspection system generates the first, second, and third images using at least two different optical modes of the one reticle inspection system. Such an inspection system may be further configured as described herein. The optical mode of the inspection system can be switched in any suitable manner (e.g., by changing the imaging NA of the system). In another embodiment, acquiring at least the first, second, and third images for the reticle includes acquiring the first, second, and third images from one or more storage media in which the first, second, and third images were stored by one or more reticle inspection systems and feeding at least the first second, and third images together to the one or more computer systems. The images can be acquired from the one or more storage media in any suitable manner. The one or more storage media may be further configured as described herein. Feeding multiple images to one or more computer systems simultaneously may be performed in any suitable manner.

Figure 2:
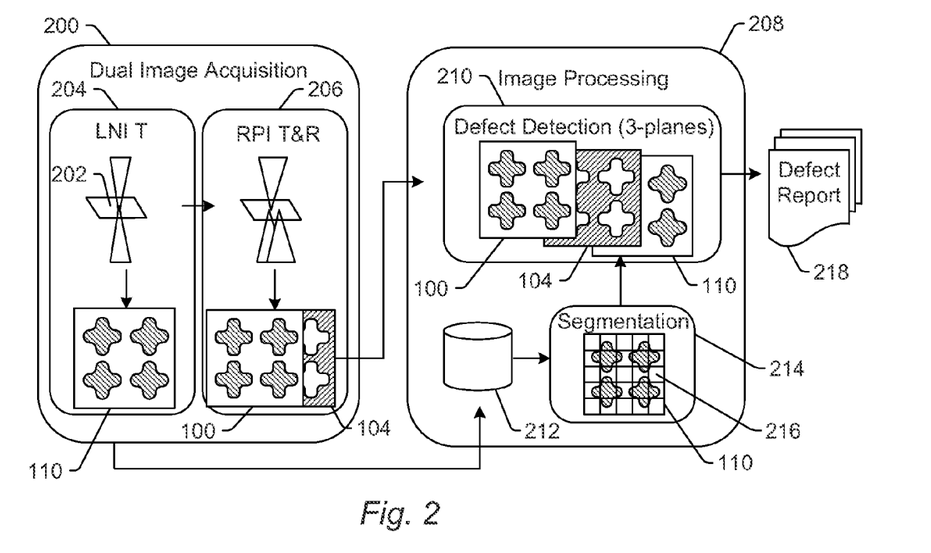
FIG. 2 is a flow chart illustrating one embodiment of a method for inspecting a reticle.

In this manner, the method may include capturing reticle plane inspection (RPI) type transmitted and reflected images followed by a third low NA inspection (LNI) type image capture (or vice versa). In one such embodiment, as shown in FIG. 2, the method may include dual image acquisition phase 200 in which reticle 202 may be imaged in LNI transmitted (LNI T) imaging step 204 to generate image 110 described further above followed by RPI transmitted and reflected (RPI T&R) step 206 to generate images 100 and 104 described further above. Imaging steps 204 and 206 may also be performed in reverse order. After all of the images have been generated, the images can be provided to one or more computer systems, such as those described further herein, for image processing phase 208. As such, one LNI image and two RPI images may be captured and processed together. The image processing phase may include defect detection step 210, which may be performed using the combination of images 100, 104, and 110. In this manner, the defect detection may be performed in 3 planes: the transmitted RPI plane, the reflected RPI plane, and the LNI transmitted plane. Defect detection may be performed as described further herein. The image processing phase shown in FIG. 2 may also include any other steps described herein.

As described above, the third image is acquired using a substantially low NA. In this manner, the third image may roughly approximate the wafer plane image of the reticle. For example, conditions other than the substantially low NA at which the third image is acquired may or may not approximate those of the exposure system. In addition, in one embodiment, the third image is further acquired with the substantially low NA and one or more additional optical conditions that are substantially the same as optical conditions used by an exposure tool to print a wafer using the reticle. Therefore, the third image may be acquired at optical conditions that simulate those of a lithography exposure system.

In instances in which the third image is not acquired at optical conditions that simulate those of an exposure system, the method may include acquiring a fourth image of the reticle at those conditions. For example, in one embodiment, the acquiring step includes acquiring a fourth image for the reticle, and the fourth image is acquired with one or more optical conditions that are substantially the same as optical conditions used by an exposure tool to print a wafer using the reticle. Such a fourth image (or second low NA image) could be captured to improve the accuracy with which the exposure system (or scanner) is emulated or to add another image for differentiating contamination from patterns for SL inspections. In another embodiment, the acquiring step includes acquiring a fourth image for the reticle, and the fourth image is acquired with the same substantially low NA as the third image, and the third and fourth images are acquired with different focus conditions. In this manner, the fourth image may be taken with the same optical conditions as the third image except at different focuses. The fourth image may be acquired in the manners described above as described below with respect to the system embodiments.

In one embodiment, detecting the defects includes aligning at least the first, second, and third images to each other. In this manner, the portions of the first, second, and third images that were generated at substantially the same locations on the reticle can be identified and used together for the defect detection step. Image registration among different image modalities is always a technical challenge. In a die-to-database (DB) inspection, we can align all the optical images to reference images generated from the database. In a die-to-die (DD) or STARlight (SL) inspection, the images must be aligned more robustly with different algorithms.

Specifically, in one embodiment, the reticle is a binary mask, detecting the defects includes aligning at least the first, second, and third images to each other, and the aligning step includes generating an additional image for the reticle by applying one or more mask pattern recovery algorithms to at least one of the first and second images, generating an aerial image for the reticle by using the additional image as input to a simulation of an exposure step performed using the reticle, and aligning the aerial image to the third image. In this manner, for binary masks (embedded phase shift masks (EPSMs), opaque MoSi over glass (OMOG) masks, chrome on glass (COG) masks, etc.), we can use the mask pattern recovery techniques described in U.S. Pat. No. 7,873,204 issued Jan. 18, 2011 to Wihl et al., U.S. Pat. No. 8,103,086 issued Jan. 24, 2012 to Shi et al., and U.S. Pat. No. 8,611,637 issued Dec. 17, 2013 to Shi et al. and PCT Application Publication Nos. WO 2008/086528 published Jul. 17, 2008 to Wihl et al., WO 2012/030825 published Mar. 8, 2013 to Shi et al., and WO 2012/030830 published Mar. 8, 2012 to Shi et al., all of which are incorporated by reference as if fully set forth herein, to generate a mask image from the first and/or second images, which is then fed forward to produce an aerial image using the LNI lithography conditions. The simulated aerial image can be aligned with the LNI image to produce alignment offsets. These offsets can then be applied to the transmitted light and reflected light images.

In an additional embodiment, the reticle is a chrome-less phase lithography (CPL) mask, detecting the defects includes aligning at least the first, second, and third images to each other, and the aligning step includes generating a pseudo-mask image for the reticle by constructing an approximated solution for the reticle from at least one of the first and second images, generating a pseudo-aerial image for the reticle by using the pseudo-mask image as input to a simulation of an exposure step performed using the reticle, and aligning the pseudo-aerial image to the third image. In this manner, for CPL masks, even though a rigorous mask pattern recovery methodology does not exist, we can construct an approximated solution that is then fed forward to produce a pseudo aerial image. This pseudo aerial image is aligned with the LNI image to produce alignment offsets that can then be applied to the RPI images.

The embodiments described herein provide a number of advantages over previously used reticle inspection methods and systems. For example, for pattern inspection modes, the embodiments described herein provide the best coverage for all defect classes capturing all DOIs in a single integrated inspection. In this manner, the embodiments described herein can be used to detect a number of different defect types in the same inspection process. In one embodiment, the defects include incorrectly formed patterned features on the reticle. In another embodiment, the defects include contamination in or on the reticle. In some embodiments, the defects include diffuse defects on the reticle. In a further embodiment, the defects include phase defects on the reticle. By processing all images at one time, information from one image can be used with any of the other images being analyzed. As such, the embodiments described herein can use three or more views in an inspection to improve coverage and overall performance.

Figure 3:
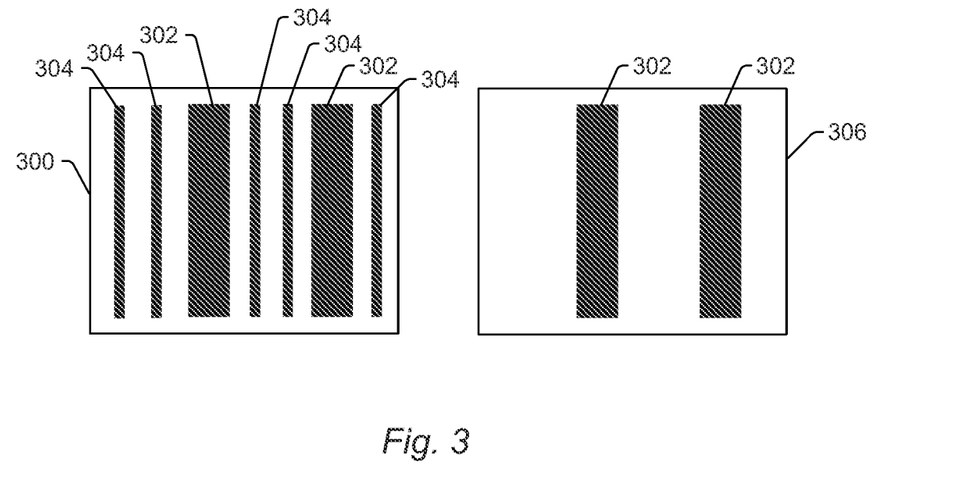
FIG. 3 is a schematic diagram illustrating a plan view of embodiments of main and assist features of a reticle.

There are a variety of ways in which the defect detection can be performed in the embodiments described herein. For example, detecting the defects may include applying a resist threshold band to the LNI image, segmenting the main and assist features, and using these regions to target sensitivity in the RPI images. In one such example, as shown in FIG. 2, the third image generated by LNI (e.g., image 110) may be used to provide segmentation information that can be stored (e.g., in database 212) and used in the image processing phase. In particular, the LNI image may be used to segment out main and assist features, and the segmentation is used subsequently for all three images to target sensitivity. These steps may be further performed as described herein. For example, the image processing phase may include performing segmentation step 214 using the segmentation information stored in database 212 to apply the segments to one or more of the first, second, and third images. (Although the segmentation step is shown in FIG. 3 as separating image 110 into a regular array or grid of segments 216, where each feature is separated into more than one segment, in reality the segmentation scheme may be much more varied and in general, a feature may be included in only one segment. In other words, in general, any one feature may not be separated into more than one segment (although there are instances in which such a situation can be envisioned).) Each of the segments may have any suitable dimensions, shapes, and any other characteristics. In addition, more than one of the same type of segment may be located at different positions across the reticle. For example, segments may be binned such that segments containing similar features are grouped into one bin while segments containing different features are grouped into different bins. As further shown in FIG. 2, the results of the segmentation step may be sent to the defect detection step, which may be performed based on the segments as described further herein. Output of the defect detection step may include one or more defect reports 218, which may be stored in one or more storage media described herein. The defect report(s) may include any information for the defects and the reticle generated by the defect detection step and any other steps performed in the image processing phase.

To describe the above concept in greater detail, detecting the defects includes, in one embodiment, applying a resist threshold band to the third image, segmenting features in the third image into main features, assist features, and other features based on results of the applying step, segmenting the first and second images based on positions of the main features, the assist features, and the other features in the third image and alignment of the third image to the first and second images thereby producing different segments for the first and second images, and detecting defects in at least two of the different segments in the first and second images with different sensitivities determined based on whether the main features or the assist and other features are located in the at least two of the different segments.

The resist threshold band may be, for instance, a threshold for a dimension of features on the reticle, where features having dimensions within that threshold band can be formed in the resist and features having dimensions beyond the threshold band cannot be formed in the resist. To illustrate these different types of reticle features further, FIG. 3 shows features that may be included on a substantially small portion of a hypothetical reticle. As such, the reticle features shown in FIG. 3 are not included herein to limit the embodiments to the illustrated reticle features. As shown in image 300, the reticle features printed on a reticle may include main reticle features 302 and assist features 304. As can be seen in image 300, the assist features have a width that is substantially smaller than the width of the main reticle features. The width of the assist features may also be smaller than the resolution limit of the resist being printed with the reticle. Therefore, the assist features will not print on the wafer, although they may "assist" or contribute to the correct printing of the main features. For example, as shown in image 306, the reticle features printed on a wafer include main reticle features 302, but not the assist features shown in image 300. As such, using a resist threshold band, main reticle features can be separated from assist features and other features on the reticle.

Therefore, based on information about which features are main features and which features are assist and other features, the areas of the reticle in the third image that contain only main features can be identified and separated from the areas of the reticle in third image that only contain assist and other non-main features. The positions of those different areas in the first and second images can then be determined based on the positional relationship between the third image and the first and second images as determined from image alignment. The first and second images can then be segmented in the same manner as the third image. Defect detection can then be performed in the first and second (and third) images based on whether the segments contain main features or assist and other features. For example, segments containing only main features can be inspected with a relatively high sensitivity while segments containing only assist and other features can be inspected with a relatively low sensitivity. The sensitivity with which the defects are detected in any one segment can be changed by altering one or more parameters (e.g., a threshold) of the defect detection algorithm(s) and/or method(s) that are applied to the images.

In another embodiment, detecting the defects includes determining if a defect detected in any one of the first, second, and third images is a real defect, a false defect, or a nuisance based on signals in at least two of the first, second, and third images. For example, the signals from two or more images may be used together to determine if a defect is real, false, or nuisance. In one such example, a potential defect detected in any one of the images may be eliminated as noise if a potential defect is not also detected at the same location in another of the images (e.g., since detects may produce signals at the same locations in more than one mode while noise may not have spatial coincidence from mode to mode). Of course, more complicated methods may be used for determining real defects, false defects, and nuisance. In another example, the embodiments described herein may use low NA and higher resolution images together to improve inspection performance and estimate the printability of defects caught. For example, for defects that are detected using the first and/or second high resolution images, the corresponding location in the third LNI image may be examined to determine if the defects (if they were even defects) have printed in the third image. If a defect does not appear in the third image, it is a safe assumption that it will not print on a wafer. Such defects will generally be of no interest to a user and therefore can advantageously be eliminated from inspection results.

In a further embodiment, detecting the defects includes detecting defects in at least one of the first, second, and third images by comparing the at least one of the first, second, and third images to a reference image for the reticle stored in a database, the reference image is generated by modeling, and detecting the defects further includes altering the modeling based on one or more of the first, second, and third images. For example, for DB type inspections, the embodiments described herein can be used to improve database modeling for a reference image by utilizing content from the additional images. In one such example, the third (LNI) images may be used as wafer plane images for the first and second (RPI) images to tune a modeling process that simulates the exposure step of the lithography process.

In an additional embodiment, detecting the defects includes altering one or more parameters of an image processing technique applied to one or more of the first, second, and third images for correcting the one or more of the first, second, and third images for reticle inspection system noise based on one or more other of the first, second, and third images. For example, the embodiments may include utilizing additional images (e.g., the third images) to improve focus compensation and other corrections resulting from tool noise.

In one embodiment, detecting the defects includes determining a defect type of a defect detected in at least one of the first, second, and third images based on a combination of two or more of the first, second, and third images. For contamination inspection, the additional images allow the algorithm to better differentiate between pattern features on the mask and contamination or other yield limiting events that should not be present. The original SL algorithm used two images and looked at the transmitted and reflected signals at each pixel to find the DOIs. By adding a third image (or more images), the algorithm can analyze the features in higher order dimensions thus improving defect detection. In other words, the embodiments described herein can use more than two images and low and high NA images to perform a higher dimensional contamination algorithm.

In some embodiments, the third image is further acquired by imaging a physical version of the reticle. For example, modeling approaches (aerial plane inspection (API), wafer plane inspection (WPI), simulated reticle plane inspection (sRPI), etc.) have been developed to take substantially high resolution images and reconstruct the wafer scanner's image in the aerial or wafer plane. These methods have the advantage of starting with higher resolution images and the ability to more accurately model the optical conditions. They are highly reliable to predict the printing impact of pattern diffused defects. The disadvantage of this type of approach is the lack of phase information needed to accurately model the materials present. Assumptions can be made but this approach breaks down with phase type masks (e.g., alternating phase shifting masks (APSM), CPL, etc.) and with foreign materials like crystal growth. Therefore, since the third images described herein are generated by imaging a physical mask (instead of by simulation), the embodiments described herein can detect many more types of defects than other reticle inspection methods and systems.

The reticle inspection performed by the embodiments described herein can be used at any point in the lifetime of a reticle. For example, the reticle inspection described herein may be performed in a mask shop during or after fabrication of the reticle itself. In addition, or alternatively, the reticle inspection may be performed in a wafer fab, between exposures of wafers with the reticle.

Each of the embodiments of the methods described above may include any other step(s) of any other method(s) described herein. Furthermore, each of the embodiments of the methods described above may be performed by any of the systems described herein.

All of the methods described herein may include storing results of one or more steps of the method embodiments in a non-transitory computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. For example, after the method has detected the defects, the method may include storing information about the detected defects in a storage medium.

Figure 4:
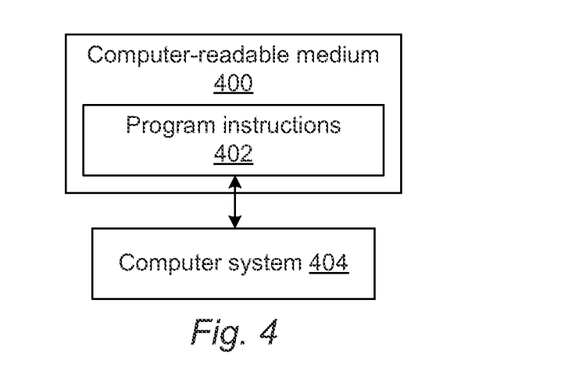
FIG. 4 is a block diagram illustrating one embodiment of a non-transitory computer-readable medium storing program instructions executable on a computer system for performing one or more of the computer-implemented methods described herein.

An additional embodiment relates to a non-transitory computer-readable medium storing program instructions executable on a computer system for performing a computer-implemented method for inspecting a reticle. One such embodiment is shown in FIG. 4. In particular, as shown in FIG. 4, non-transitory computer-readable medium 400 includes program instructions 402 executable on computer system 404. The computer-implemented method includes the steps of the method described above. The computer-implemented method for which the program instructions are executable may include any other step(s) described herein.

Program instructions 402 implementing methods such as those described herein may be stored on computer-readable medium 400. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

The computer system may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer system may also include any suitable processor known in the art such as a parallel processor. In addition, the computer system may include a computer platform with high speed processing and software, either as a standalone or a networked tool.

Figure 5:
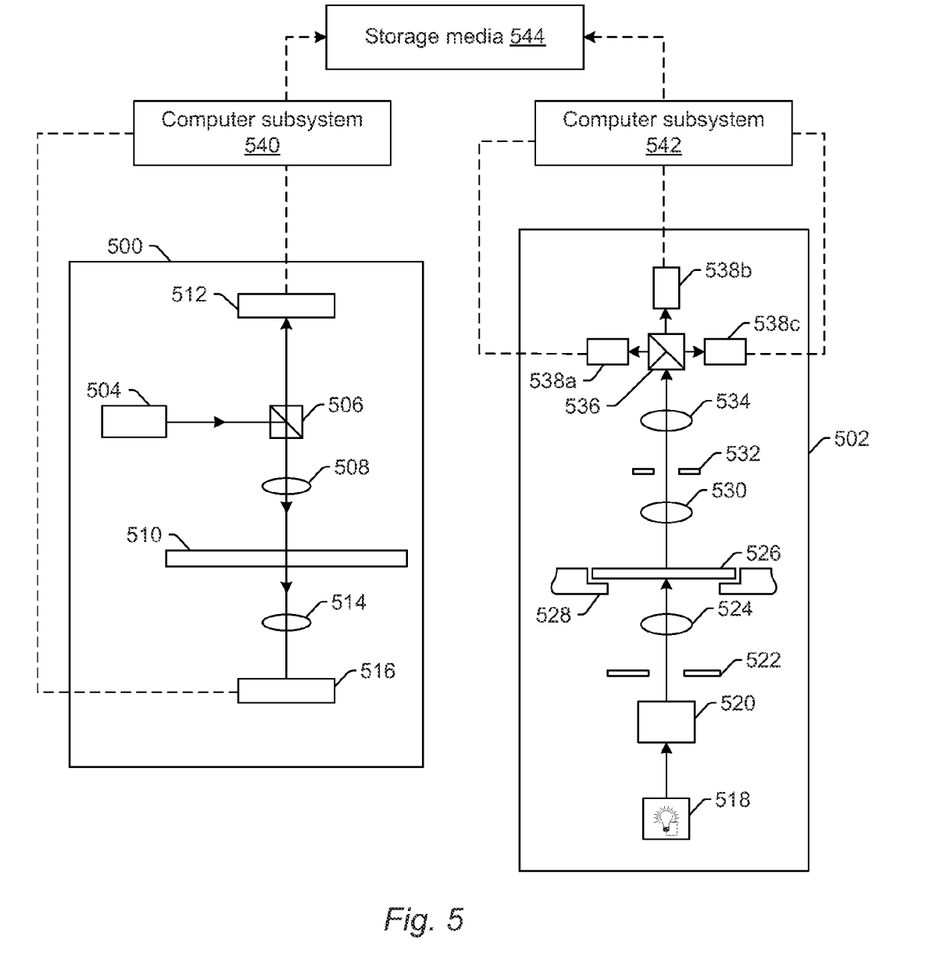
FIG. 5 is a schematic diagram illustrating a side view of one embodiment of a reticle inspection system.

Another embodiment relates to a reticle inspection system. One embodiment of such a system is shown in FIG. 5. The reticle inspection system includes one or more optical subsystems configured to acquire at least first, second, and third images for the reticle. The first, second, and third images may be any of such images described further herein. As shown in FIG. 5, the reticle inspection system includes optical subsystems 500 and 502. Although the reticle inspection system is shown in FIG. 5 as including two optical subsystems, it is to be understood that the reticle inspection system may include only one such optical subsystem if it can be configured to generate all of the images described herein (e.g., by changing the resolution or NA at which images of the reticle are generated).

As further shown in FIG. 5, optical subsystem 500 includes light source 504. Light source 504 may include any suitable light source known in the art such as a laser. Light source 504 is configured to direct light to beam splitter 506, which is configured to reflect the light from light source 504 to refractive optical element 508. Refractive optical element 508 is configured to focus light from beam splitter 506 to reticle 510. Beam splitter 506 may include any suitable beam splitter such as a 50/50 beam splitter. Refractive optical element 508 may include any suitable refractive optical element, and although refractive optical element 508 is shown in FIG. 5 as a single refractive optical element, it may be replaced with one or more refractive optical elements and/or one or more reflective optical elements.

Light source 504, beam splitter 506, and refractive optical element 508 may, therefore, form an illumination channel for the optical subsystem. The illumination channel may include any other suitable elements (not shown in FIG. 5) such as one or more polarizing components, diffractive optical elements (DOEs), and one or more filters such as spectral filters. As shown in FIG. 5, the light source, beam splitter, and refractive optical element are configured such that the light is directed to the reticle at a normal or substantially normal angle of incidence. The optical subsystem may be configured to scan the light over the reticle in any suitable manner.

Light reflected from reticle 510 due to illumination may be collected by refractive optical element 508 and directed through beam splitter 506 to detector 512. Therefore, the refractive optical element, beam splitter, and detector may form a detection channel of the optical subsystem. The detector may include any suitable imaging detector known in the art such as a charge coupled device (CCD) or time-delayed integrator (TDI). This detection channel may also include one or more additional components (not shown in FIG. 5) such as one or more polarizing components, one or more spatial filters, one or more spectral filters, and the like. Detector 512 is configured to generate output that is responsive to the reflected light detected by the detector. The output may include signals, signal data, images, image data, and any other suitable output. In addition, the output preferably includes a substantially high resolution image of light reflected by the reticle. In other words, detector 512 generates the second images described herein.

Light transmitted by reticle 510 due to illumination may be collected by refractive optical element 514 and directed to detector 516. Therefore, the refractive optical element and detector may form a detection channel of the optical subsystem. The detector may include any suitable imaging detector known in the art such as a CCD. This detection channel may also include one or more additional components (not shown in FIG. 5) such as one or more polarizing components, one or more spatial filters, one or more spectral filters, and the like. Detector 516 is configured to generate output that is responsive to the transmitted light detected by the detector. The output may include signals, signal data, images, image data, and any other suitable output. In addition, the output preferably includes a substantially high resolution image of light transmitted by the reticle. In other words, detector 516 generates the first images described herein.

The optical subsystem may be configured to have more than one mode in any suitable manner. In some instances, the optical subsystem can have more than one mode sequentially (e.g., by changing one or more parameters of an imaging lens of the optical subsystem such as NA between scans of a reticle). Furthermore, the optical subsystem can have some modes simultaneously and other modes sequentially. The reticle inspection system may be configured to control the optical mode(s) used for any scan of any reticle in any suitable manner.

As further shown in FIG. 5, optical subsystem 502 includes an illumination subsystem and a collection subsystem as described in more detail herein. The illumination subsystem includes light source 518. Light source 518 may be a coherent light source such as a laser. The light source may be configured to emit monochromatic light having a wavelength of about 248 nm, about 193 nm, about 157 nm, or another ultraviolet wavelength. Alternatively, the light source may be configured to emit light have a range of wavelengths and may be coupled to a spectral filter (not shown). An example of a broadband light source includes, but is not limited to, a He—Xe arc lamp that generates light in the deep ultraviolet wavelength regime. In this manner, the light source and the filter may emit monochromatic light having a wavelength as described above. The light source and the filter may be configured such that different wavelengths of light may be emitted from the light source and the filter depending upon, for example, the type of reticle being inspected or the type of inspection or measurement being performed. The light source may also be configured to emit light other than ultraviolet light. In addition, the light source may be configured to emit light continuously or at various time intervals in pulses.

The illumination subsystem may also include a number of optical components coupled to the light source. For example, light from light source 518 may first pass through homogenizer 520. Homogenizer 520 may be configured to reduce speckle of the light from the light source. The illumination subsystem may also include aperture 522. Aperture 522 may have an adjustable NA. For example, the aperture my be coupled to a control mechanism that may be configured to mechanically alter the aperture depending upon a control signal received from a user or from program instructions received from a program recipe being run on the system. In this manner, the light may have various partial coherence factors, $\sigma$. For example, aperture 522 may be altered to adjust a pupil of condenser lens 524. The pupil of the condenser lens controls the NA of the system. As the pupil of the condenser is reduced, coherence of the illumination increases thereby decreasing the value of $\sigma$. The value of $\sigma$ may be expressed as the ratio of the NA of the condenser lens to the NA of the objective lens. Exposure systems may have a value of $\sigma$ in a range between about 0.3 to about 0.9. Therefore, aperture 522 may be altered such that the optical subsystem has a value of $\sigma$ between about 0.3 and about 0.9. The value of $\sigma$ may be altered depending upon the features on the reticle. For example, a higher value for $\sigma$ may be used if the reticle includes lines and spaces than if the reticle includes contact holes. The control mechanism may also be configured to alter the aperture to provide annular or off-axis illumination. The aperture may also be configured to provide other types of illumination such as quadrapole or dipolar illumination. The aperture may be further configured to alter a shape of the beam of light. For example, the aperture may be a diffraction optical element or an apodization aperture.

The illumination subsystem may also include a number of additional optical components (not shown). For example, the illumination subsystem may also include a telescope configured to alter the beam diameter of the light. In addition, the illumination subsystem may include one or more relay lenses, additional lenses such as a field lens, folding mirrors, additional apertures, and beamsplitters.

The illumination subsystem may also include condenser lens 524. Condenser lens 524 may be configured to alter a diameter of the light in the object (reticle) plane to approximately, or greater than, the field of view of the system. Light exiting the condenser lens may illuminate reticle 526 supported upon stage 528. The stage is configured to support the reticle by contacting the reticle proximate outer lateral edges of the reticle. An opening in the stage is provided to allow light from the illumination subsystem to illuminate the reticle. Stage 528 may be configured to move the reticle such that an alignment of the reticle may be altered and such that light may scan across the reticle. Alternatively, the illumination system may include a scanning element (not shown) such as an acousto-optical deflector or a mechanical scanning assembly such at the reticle may remain substantially stationary while the light is scanned across the reticle. Stage 528 may also be configured to move the reticle through focus thereby altering a focus setting of the optical subsystem. The stage may also be coupled to an autofocusing device (not shown) that is configured to alter a position of the stage thereby altering a position of the reticle to maintain a focus setting of the optical subsystem during an inspection. Alternatively, an autofocusing device may be coupled to the objective lens to alter a position of the objective lens to maintain the focus setting during an inspection.

The optical subsystem may also include a number of optical components arranged to form a collection subsystem. For example, the collection subsystem includes objective lens 530. Light transmitted by the reticle is collected by objective lens 530. The collection subsystem also includes aperture 532 having an adjustable NA. The NA of aperture 532 may also be selected such that light exiting the aperture has a selected magnification. Aperture 532 is positioned between objective lens 530 and lens 534, which may be configured as a tube lens. Light from lens 534 may be directed to beamsplitter 536. Beamsplitter 536 may be configured to direct the light to three detectors 538a, 538b, and 538c. The collection subsystem may also include a number of additional optical components (not shown) such as a magnification lens. The magnification lens may be positioned between lens 534 and the beamsplitter.

Detectors 538a, 538b, and 538c may be configured to form an image of the light transmitted by an illuminated portion of the reticle. Such an image may be referred to as an "aerial image." The detectors should also be sensitive to at least one of the wavelengths of light described above. The detectors, however, may also be sensitive to a range of wavelengths in the deep ultraviolet regime in addition to wavelengths in other regimes. The detectors may include, for example, CCDs or TDI cameras. The detectors may also have a one-dimensional or two-dimensional array of pixels. Each of the three detectors may have a different focus setting. In this manner, the three detectors may form images of the reticle at three different focus settings substantially simultaneously. For example, one detector may be substantially in focus, and the other two detectors may be out of focus in opposite directions with respect to the in-focus condition. In addition, the optical subsystem may include any number of such detectors depending on the mechanical or physical constraints of the optical subsystem.

Alternatively, the optical subsystem may only include one detector configured to form an image of the reticle. The detector may have a focus setting approximately equal to a focus setting of an exposure system. Images of the reticle at different focus settings may be formed by forming a plurality of images of the reticle and altering the focus setting of the detector after each image is formed. In such an embodiment, beamsplitter 536 would not be necessary to split the light to multiple detectors.

The reticle inspection system may include a number of other components that are not shown in FIG. 5. For example, the system may include a load module, an alignment module, a handler such as a robotic transfer arm, and an environmental control module and may include any such components known in the art.

As described above, the optical subsystem may be configured to form an aerial image of the reticle using a set of exposure conditions. The exposure conditions include, but are not limited to, wavelength of illumination, coherence of illumination, shape of the beam of illumination, NA, and focus settings. The set of exposure conditions may be selected to be substantially equivalent to exposure conditions used by an exposure system to print an image of the reticle onto a wafer. Therefore, an aerial image formed by optical subsystem 502 may be substantially optically equivalent to an image of the reticle that would be printed on a wafer by the exposure system under the set of exposure conditions.

The reticle inspection system also includes one or more computer subsystems configured for detecting defects on the reticle using at least the first, second, and third images for the reticle in combination. The computer subsystem(s) may be configured to detect the defects as described further herein. In one embodiment, as shown in FIG. 5, the reticle inspection system includes computer subsystems 540 and 542 (although computer subsystems 540 and 542 may be replaced with a single computer subsystem if it can perform the steps described further herein). In the embodiment shown in FIG. 5, computer subsystem 540 is coupled to optical subsystem 500. For example, the computer subsystem may be coupled to a detector of the optical subsystem. In one such example, as shown in FIG. 5, computer subsystem 540 is coupled to detectors 512 and 516 of optical subsystem 500 (e.g., by one or more transmission media shown by the dashed lines in FIG. 5, which may include any suitable transmission media known in the art). The computer subsystem may be coupled to the detectors in any suitable manner. The computer subsystem may be coupled to the optical subsystem in any other suitable manner such that image(s) and any other information for the reticle generated by the optical subsystem can be sent to the computer subsystem and, optionally, such that the computer subsystem can send instructions to the optical subsystem to perform one or more steps described herein.

In a similar manner, computer subsystem 542 is coupled to optical subsystem 502. For example, the computer subsystem may be coupled to a detector of the optical subsystem. In one such example, as shown in FIG. 5, computer subsystem 542 is coupled to detectors 538a, 538b, and 538c of optical subsystem 502 (e.g., by one or more transmission media shown by the dashed lines in FIG. 5, which may include any suitable transmission media known in the art). The computer subsystem may be coupled to the detectors in any suitable manner. The computer subsystem may be coupled to the optical subsystem in any other suitable manner such that image(s) and any other information for the reticle generated by the optical subsystem can be sent to the computer subsystem and, optionally, such that the computer subsystem can send instructions to the optical subsystem to perform one or more steps described herein.

The computer subsystem(s) included in the system may also include a computer subsystem (not shown) that is not coupled to an optical subsystem. In this manner, one of the computer subsystems may be a stand alone type computer subsystem, which may be coupled to the computer subsystems shown in FIG. 5. For example, a stand alone type computer subsystem may be configured to acquire the images described herein and to perform other steps described herein. In one such example, computer subsystems 540 and 542 may be configured to store images received from their respectively coupled optical subsystems and to store the images in storage media 544, which may be further configured as described above. The stand alone type computer subsystem may then acquire the images from the storage media and perform one or more steps using some combination of the images.

It is noted that FIG. 5 is provided herein to generally illustrate one configuration of optical subsystems that may be included in the reticle inspection system embodiments described herein. Obviously, the configuration of the optical subsystems described herein may be altered to optimize the performance of the system as is normally performed when designing a commercial inspection system. In addition, the reticle inspection systems described herein may be implemented using an existing optical subsystem (e.g., by adding functionality described herein to an existing inspection system) such as the reticle inspection tools that are commercially available from KLA-Tencor, Milpitas, Calif. For some such systems, the methods described herein may be provided as optional functionality of the system (e.g., in addition to other functionality of the system). Alternatively, the reticle inspection systems described herein may be designed "from scratch" to provide a completely new system.

Further modifications and alternative embodiments of various aspects of the invention will be apparent to those skilled in the art in view of this description. For example, methods and systems for inspecting a reticle are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for inspecting a reticle, comprising:
acquiring at least first, second, and third images for the reticle, wherein the first image is a substantially high resolution image of light transmitted by the reticle, wherein the second image is a substantially high resolution image of light reflected from the reticle, and wherein the third image is an image of light transmitted by the reticle that is acquired with a substantially low numerical aperture; and
detecting defects on the reticle using at least the first, second, and third images for the reticle in combination, wherein detecting the defects comprises applying a resist threshold band to the third image, segmenting features in the third image into main features, assist features, and other features based on results of said applying, segmenting the first and second images based on positions of the main features, the assist features, and the other features in the third image and alignment of the third image to the first and second images thereby producing different segments for the first and second images, and detecting defects in at least two of the different segments in the first and second images with different sensitivities determined based on whether the main features or the assist and other features are located in the at least two of the different segments, and wherein the acquiring and detecting steps are performed with one or more computer systems.

2. The method of claim 1, wherein said acquiring comprises acquiring the first and second images from one reticle inspection system and acquiring the third image from another reticle inspection system.

3. The method of claim 1, wherein said acquiring comprises acquiring the first, second, and third images from one reticle inspection system, and wherein the one reticle inspection system generates the first, second, and third images using at least two different optical modes of the one reticle inspection system.

4. The method of claim 1, wherein said acquiring comprises acquiring the first, second, and third images from one or more storage media in which the first, second, and third images were stored by one or more reticle inspection systems and feeding at least the first, second, and third images together to the one or more computer systems.

5. The method of claim 1, wherein the third image is further acquired with the substantially low numerical aperture and one or more additional optical conditions that are substantially the same as optical conditions used by an exposure tool to print a wafer using the reticle.

6. The method of claim 1, wherein the third image is further acquired by imaging a physical version of the reticle.

7. The method of claim 1, wherein the defects comprise incorrectly formed patterned features on the reticle.

8. The method of claim 1, wherein the defects comprise contamination in or on the reticle.

9. The method of claim 1, wherein the defects comprise diffuse defects on the reticle.

10. The method of claim 1, wherein the defects comprise phase defects on the reticle.

11. The method of claim 1, wherein said acquiring further comprises acquiring a fourth image for the reticle, and wherein the fourth image is acquired with one or more optical conditions that are substantially the same as optical conditions used by an exposure tool to print a wafer using the reticle.

12. The method of claim 1, wherein said acquiring further comprises acquiring a fourth image for the reticle, wherein the fourth image is acquired with the same substantially low numerical aperture as the third image, and wherein the third and fourth images are acquired with different focus conditions.

13. The method of claim 1, wherein the reticle is a binary mask, wherein detecting the defects further comprises aligning at least the first, second, and third images to each other, and wherein said aligning comprises generating an additional image for the reticle by applying one or more mask pattern recovery algorithms to at least one of the first and second images, generating an aerial image for the reticle by using the additional image as input to a simulation of an exposure step performed using the reticle, and aligning the aerial image to the third image.

14. The method of claim 1, wherein the reticle is a chrome-less phase lithography mask, wherein detecting the defects further comprises aligning at least the first, second, and third images to each other, and wherein said aligning comprises generating a pseudo-mask image for the reticle by constructing an approximated solution for the reticle from at least one of the first and second images, generating a pseudo-aerial image for the reticle by using the pseudo-mask image as input to a simulation of an exposure step performed using the reticle, and aligning the pseudo-aerial image to the third image.

15. The method of claim 1, wherein detecting the defects further comprises determining if a defect detected in any one of the first, second, and third images is a real defect, a false defect, or a nuisance based on signals in at least two of the first, second, and third images.

16. The method of claim 1, wherein said detecting further comprises detecting defects in at least one of the first, second, and third images by comparing the at least one of the first, second, and third images to a reference image for the reticle stored in a database, wherein the reference image is generated by modeling, and wherein said detecting further comprises altering the modeling based on one or more of the first, second, and third images.

17. The method of claim 1, wherein said detecting further comprises altering one or more parameters of an image processing technique applied to one or more of the first, second, and third images for correcting the one or more of the first, second, and third images for reticle inspection system noise based on one or more other of the first, second, and third images.

18. The method of claim 1, wherein said detecting further comprises determining a defect type of a defect detected in at least one of the first, second, and third images based on a combination of two or more of the first, second, and third images.

19. A non-transitory computer-readable medium, storing program instructions executable on a computer system for performing a computer-implemented method for inspecting a reticle, wherein the computer-implemented method comprises:

acquiring at least first, second, and third images for the reticle, wherein the first image is a substantially high resolution image of light transmitted by the reticle, wherein the second image is a substantially high resolution image of light reflected from the reticle, and wherein the third image is an image of light transmitted by the reticle that is acquired with a substantially low numerical aperture; and detecting defects on the reticle using at least the first, second, and third images for the reticle in combination, wherein the detecting the defects comprises applying a resist threshold band to the third image, segmenting features in the third image into main features, assist features, and other features based on results of said applying, segmenting the first and second images based on positions of the main features, the assist features, and the other features in the third image and alignment of the third image to the first and second images thereby producing different segments for the first and second images, and detecting defects in at least two of the different segments in the first and second images with different sensitivities determined based on whether the main features or the assist and other features are located in the at least two of the different segments.

20. A reticle inspection system, comprising:

one or more optical subsystems configured to acquire at least first, second, and third images for the reticle, wherein the first image is a substantially high resolution image of light transmitted by the reticle, wherein the second image is a substantially high resolution image of light reflected from the reticle, and wherein the third image is an image of light transmitted by the reticle that is acquired with a substantially low numerical aperture; and one or more computer subsystems configured for detecting defects on the reticle using at least the first, second, and third images for the reticle in combination, wherein detecting the defects comprises applying a resist threshold band to the third image, segmenting features in the third image into main features, assist features, and other features based on results of said applying, segmenting the first and second images based on positions of the main features, the assist features, and the other features in the third image and alignment of the third image to the first and second images thereby producing different segments for the first and second images, and detecting defects in at least two of the different segments in the first and second images with different sensitivities determined based on whether the main features or the assist and other features are located in the at least two of the different segments.

21. The reticle inspection system of claim 20, wherein the first and second images are acquired by one of the one or more optical subsystems and the third image is acquired by another of the one or more optical subsystems.

22. The reticle inspect on system of claim 20, wherein the first, second, and third images are acquired by one of the one or more optical subsystems, and wherein the one of the one or more optical subsystems generates the first, second, and third images using at least two different optical modes of the one of the one or more optical subsystems.

23. The reticle inspection system of claim 20, wherein the reticle inspection system is configured to store the first, second, and third images in one or more storage media and to feed at least the first, second, and third images together to the one or more computer systems.

24. The reticle inspection system of claim 20, wherein the third image is further acquired with the substantially low numerical aperture and one or more additional optical conditions that are substantially the same as optical conditions used by an exposure tool to print a wafer using the reticle.

25. The reticle inspection system of claim 20, wherein the third image is further acquired by imaging a physical version of the reticle.

26. The reticle inspection system of claim 20, wherein the defects comprise incorrectly formed patterned features on the reticle.

27. The reticle inspection system of claim 20, wherein the defects comprise contamination in or on the reticle.

28. The reticle inspection system of claim 20, wherein the defects comprise diffuse defects on the reticle.

29. The reticle inspection system of claim 20, wherein the defects comprise phase defects on the reticle.

30. The reticle inspection system of claim 20, wherein the one or more optical subsystems are further configured to acquire a fourth image for the reticle, and wherein the fourth image is acquired with one or more optical conditions that are substantially the same as optical conditions used by an exposure tool to print a wafer using the reticle.

31. The reticle inspection system of claim 20, wherein the one or more optical subsystems are further configured to acquire a fourth image for the reticle, wherein the fourth image is acquired with the same substantially low numerical aperture as the third image, and wherein the third and fourth images are acquired with different focus conditions.

32. The reticle inspection system of claim 20, wherein the reticle is a binary mask, wherein detecting the defects further comprises aligning at least the first, second, and third images to each other, and wherein said aligning comprises generating an additional image for the reticle by applying one or more mask pattern recovery algorithms to at least one of the first and second images, generating an aerial image for the reticle by using the additional image as input to a simulation of an exposure step performed using the reticle, and aligning the aerial image to the third image.

33. The reticle inspection system of claim 20, wherein the reticle is a chrome-less phase lithography mask, wherein detecting the defects further comprises aligning at least the first, second, and third images to each other, and wherein said aligning comprises generating a pseudo-mask image for the reticle by constructing an approximated solution for the reticle from at least one of the first and second images, generating a pseudo-aerial image for the reticle by using the pseudo-mask image as input to a simulation of an exposure step performed using the reticle, and aligning the pseudo-aerial image to the third image.

34. The reticle inspection system of claim 20, wherein detecting the defects further comprises determining if a defect detected in any one of the first, second, and third images is a real defect, a false defect, or a nuisance based on signals in at least two of the first, second, and third images.

35. The reticle inspection system of claim 20, wherein said detecting further comprises detecting defects in at least one of the first, second, and third images by comparing the at least one of the first, second, and third images to a reference image for the reticle stored in a database, wherein the reference image is generated by modeling, and wherein said detecting further comprises altering the modeling based on one or more of the first, second, and third images.

36. The reticle inspection system of claim 20, wherein said detecting further comprises altering one or more parameters of an image processing technique applied to one or more of the first, second, and third images for correcting the one or more of the first, second, and third images for reticle inspection system noise based on one or more other of the first, second, and third images.

37. The reticle inspection system of claim 20, wherein said detecting further comprises determining a defect type of a defect detected in at least one of the first, second, and third images based on a combination of two or more of the first, second, and third images.

* * * * *